United States Patent [19]

Katoh et al.

[11] Patent Number: 5,322,845

[45] Date of Patent: Jun. 21, 1994

[54] ACRYLIC ACID DERIVATIVES, A FUNGICIDE CONTAINING THEM AS AN ACTIVE INGREDIENT, AND INTERMEDIATE COMPOUNDS THEREOF

[75] Inventors: Tsuguhiro Katoh; Atsuo Mizuguchi; Hirotaka Takano, all of Hyogo, Japan

[73] Assignee: Sumitomo Chemical Company, Limited, Osaka, Japan

[21] Appl. No.: 955,040

[22] Filed: Oct. 1, 1992

[30] Foreign Application Priority Data

Oct. 2, 1991 [JP] Japan .................................. 3-255132

[51] Int. Cl.$^5$ ...................... A61K 31/44; A61K 31/53; C07D 401/10; C07D 403/10

[52] U.S. Cl. ..................................... 514/242; 514/255; 514/256; 514/335; 514/338; 514/340; 514/342; 544/182; 544/216; 544/239; 544/254; 544/255; 544/316; 544/405; 546/141; 546/153; 546/261; 546/270; 546/280; 546/283; 546/284; 546/298

[58] Field of Search ............... 546/261, 298, 270, 141, 546/153, 280, 283, 284; 71/94; 514/335, 338, 340, 342, 242, 255, 256; 544/182, 216, 239, 254, 255, 316, 405

[56] References Cited

FOREIGN PATENT DOCUMENTS 0312243 4/1989 European Pat. Off. .
0350691 1/1990 European Pat. Off. .

*Primary Examiner*—Marianne M. Cintins
*Assistant Examiner*—Phyllis G. Spivack
*Attorney, Agent, or Firm*—Sughrue, Mion, Zinn, Macpeak & Seas

[57] ABSTRACT

An acrylic acid compound useful for fungicides is provided. The compound has the following formula (I)

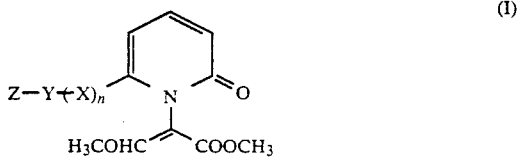

wherein X represents a phenyl group which may be substituted, or a methylene group, n represents 0 or 1, Y represents an oxygen atom or a sulfur atom, Z represents a phenyl group, an aralkyl group, an aromatic heterocyclyl group or an aromatic heterocyclylmethylene group and Z may be substituted.

23 Claims, No Drawings

ACRYLIC ACID DERIVATIVES, A FUNGICIDE CONTAINING THEM AS AN ACTIVE INGREDIENT, AND INTERMEDIATE COMPOUNDS THEREOF

This invention relates to a novel acrylic acid derivative, a method for preparation thereof and a fungicide containing it as an active ingredient.

Certain kinds of acrylic acid derivatives are known to be useful as an active ingredient of fungicides (cf., JP2-121970A). However, their fungicidal potency is not always sufficiently high, so that they can not be said to be always satisfactory.

An object of the present invention is to provide a compound having preventive and curative controlling effects against many plant diseases.

The present inventors have found that acrylic acid derivatives having the formula (I) mentioned below or their salts (hereinafter referred simply to as the present compound) have excellent fungicidal activity:

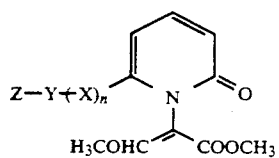

(I)

wherein X represents a phenyl group which may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, or a methylene group, n represents 0 or 1, Y represents an oxygen atom or a sulfur atom, Z represents a phenyl group, an aralkyl group, an aromatic heterocyclic group or an aromatic heterocyclic methylene group and Z may be substituted with one to three identical or different lower alkyl groups, lower alkenyl groups, lower alkynyl groups, lower alkoxy groups, lower haloalkyl groups, lower haloalkoxy groups, cycloalkyl groups, lower alkylthio groups, lower haloalkylthio groups or halogen atoms, or may be substituted with one substituent R in which R represents a phenyl group, a phenoxy group, an aralkyl group, an aralkyloxy group, an aromatic heterocyclic group, an aromatic heterocyclic oxy group or an aromatic heterocyclic methylene group and R may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms. In the above formula [I], the term "lower" generally means "having 1 to 5 carbon atoms".

Examples of $C_1$-$C_5$ alkyl group are methyl, ethyl, propyl, isopropyl, butyl, isobutyl, tertbutyl, pentyl, etc.

Examples of a $C_2$-$C_5$ alkenyl group are allyl, propenyl, isopropenyl, 1-butenyl, 2-butenyl, 2-pentenyl, 3-pentenyl, etc.

Examples of a $C_2$-$C_5$ alkynyl group are propargyl, 1-methyl-2-propargyl, 1-butynyl, 2-butynyl, 2-pentenyl, 3-pentenyl, etc.

Examples of a $C_1$-$C_5$ alkoxy group are methoxy, ethoxy, n-propoxy, isopropoxy, n-butoxy, isobutoxy, pentyloxy, etc.

Examples of a halo $C_1$-$C_5$ alkyl group are trifluoromethyl, difluoromethyl, bromodifluoromethyl, chlorodifluoromethyl, monofluoromethyl, trichloromethyl, 2,2,2-trifluoroethyl, 1,1,2,2-tetrafluoroethyl, 2-bromo-1,1,2,2-tetrafluoroethyl, 2-chloro-1,1,2,2-tetrafluoroethyl, heptafluoropropyl, hexafluoroisopropyl, etc.

Examples of a halo $C_1$-$C_5$ alkoxy group are trifluoromethoxy, difluoromethoxy, bromodifluoromethoxy, chlorodifluoromethoxy, monofluoromethoxy, trichloromethoxy, 2,2,2-trifluoroethoxy, 1,1,2,2-tetrafluoroethoxy, 2-bromo-1,1,2,2-tetrafluoroethoxy, 2-chloro-1,1,2,2-tetrafluoroethoxy, heptafluoropropoxy, hexafluoroisopropoxy, etc.

Examples of a halo $C_1$-$C_5$ alkylthio group are trifluoromethylthio, difluoromethylthio, bromodifluoromethylthio, chlorodifluoroethylthio, 2,2,2-trifluoromethylthio, monofluoromethylthio, 2,2,2-trifluoroethylthio 1,1,2,2-tetrafluoroethylthio, heptafluoroporpylthio, etc.

In a halo $C_1$-$C_5$ alkyl, a halo $C_1$-$C_5$ alkoxy, a halo $C_1$-$C_5$ alkylthio group, the number of halogen atom is less than 11, and the halogen may be the same or different.

Examples of a $C_1$-$C_5$ alkylthio group are methylthio, ethylthio, propylthio, isopropylthil, butylthio, pentylthio, etc.

Examples of a $C_3$-$C_5$ cycloalkyl group are cyclopropyl, cyclobutyl, cyclopentyl, etc.

Examples of halogen atoms are fluoro, bromo, chloro, iodo atom.

Preferably, the $C_1$-$C_5$ alkyl groups include methyl and ethyl groups, the $C_2$-$C_5$ alkenyl groups include an allyl group, the $C_2$-$C_5$ alkynyl groups include a propargyl group, the $C_1$-$C_5$ alkoxy groups include a methoxy group, the $C_1$-$C_5$ haloalkyl groups include a trifluoromethyl group, the $C_1$-$C_5$ haloalkoxy groups include a trifluoromethoxy group, a 1,1,2,2-tetrafluoroethoxy group, a difluoromethoxy group and a 2,2,2-trifluoroethoxy group, the $C_1$-$C_5$ alkylthio groups include a methylthio group, the $C_1$-$C_5$ haloalkylthio groups include a trifluoromethylthio group and a 1,1,2,2-tetrafluoroethylthio group, the $C_3$-$C_5$ cycloalkyl groups include a cyclopropyl group and the halogen atoms include fluorine, chlorine and bromine atoms.

The aromatic heterocyclyl groups, aromatic heterocyclyloxy groups and aromatic heterocyclylmethylene groups include aromatic heterocycle sites. Examples of the aromatic heterocycle site are pyridinyl, pyrimidinyl, pyrazinyl, pyridazinyl, 1,2,3-triazinyl, 1,2,4-triazinyl and 1,3,5-triazinyl, 1,2,4,5-tetrazinyl, furyl, thienyl, pyrrolyl, isoxazolyl, isothiazolyl, oxazolyl, thiazolyl, imidazolyl, pyrazolyl, 1,2,3-triazolyl, 1,2,4-triazolyl, tetrazolyl, quinolinyl, isoquinolinyl, quinoxalinyl, benzofuryl, benzothienyl, benzoxazolyl, benzothiazolyl, benzoisoxazolyl, benzoisothiazolyl, indolyl, benzopyrazolyl, pyrazolopyrimidinyl, triazolopyrimidinyl, pyrazolopyridinyl and triazolopyridinyl.

Examples of the aralkyl groups are a benzyl group and a phenethyl group.

The suffix n is preferably one.

The symbol X is preferably a phenyl group which may be substituted with one or two identical or different $C_1$-$C_5$ alkyl, $C_2$-$C_5$ alkenyl, $C_{2-5}$ alkynyl, $C_1$-$C_5$ alkoxy, $C_1$-$C_5$ haloalkyl, $C_{1-5}$ haloalkoxy, $C_1$-$C_5$ alkylthio and $C_1$-$C_5$ haloalkylthio groups or halogen atoms. More preferably, the phenyl group may be substituted with one or two identical or different $C_1$-$C_5$ alkyl or $C_1$-$C_5$ haloalkyl groups or halogen atoms. Further preference is a phenyl group which may be substituted with one or two identical or different $C_1$-$C_2$ alkyl groups, a trifluoromethyl group or halogen atoms. More preferably X is a phenyl group.

Y is preferably an oxygen atom.

Z is preferably a phenyl group, an aralkyl group, an aromatic heterocyclyl group or an aromatic heterocyclylmethylene group, all of which may be substituted with one to three identical or different a $C_{1-5}$ alkyl group, a $C_{1-5}$ haloalkyl group, a $C_{1-5}$ haloalkoxy group or halogen atoms. Further preference is a phenyl group, a benzyl group, a pyridyl group, a pyrimidinyl group, a pyrazinyl group or a pyridinylmethylene group, all of which may be substituted with one to three identical or different $C_{1-2}$ alkyl group or halogen atoms. More preferably, Z is a pyridyl group, pyridinylmethylene group, phenyl or a benzyl group, more preferably Z is a pyridyl or pyridinylmethylene group.

More preferably, X is a phenyl group, Y is an oxygen atom and Z is a pyridyl group, or pyridinylmethylene group.

When X is an optionally substituted phenyl group, a (Z-Y) group is preferably at meta or para position.

The compound of the present invention has a methyl methoxypropenoate group as a partial structure and includes two isomers derived from the unsymmetrical substitution double bond.

Ratio of these two isomers in the product in the process for production according to the present invention usually varies depending on individual compounds or reaction conditions, but these isomers are produced at the same time. (E) isomer is usually more than (Z) isomer in the production ratio and beside, is more active as controlling agents against plant diseases. (E) isomer is able to separate from (Z) isomer by purification means such as chromatography. All of (E) isomer, (Z) isomer and mixtures of (E) isomer and (Z) isomer are included in the present invention. (The terms "(E)" and "(Z)" used here are as defined by the well known Carn-Ingold-Prelog system.)

The compound of the present invention has preventive, curative and systemic controlling effects against many plant diseases. The following are plant diseases on which the present compound has a controlling effect; rice: *Pyricularia oryzae, Cochliobolus miyabeanus, Rhizoctonia solani*, barley and wheat: *Erysiphe graminis*, f. SP. hordei, f. SP. tritici, *Gibberella zeae, Puccinia striiformis, P. graminis, P. recodita, P. hordei*, Typhhula sp., *Micronectriella nivalis, Ustilago tritici, U. nuda, Tilletia caries, Pseudocercosporella herpotrichoids, Rhynchosporium secalis, Septoria tritici, Leptosphaeria nodorum*, citrus: *Diaporthe citri, Elsinoe fawcetti, Penicillium digitatum, P. italicum*, apple: *Sclerotinica mail, Valsa mali, Podpsphaera leucotricha, Alternaria mali, Venturia inaequalis*, pear: *Venturia nashicola, V. pirina, Alternaria kikuchiana, Gymnosporangium haraeanum*, peach: *Sclerotinia cinerea, Cladosporium carpophilum, Phomopsis sp.*, grape: *Elsinoe ampelina, Glomerella cingulata, Uncinula necator, Phakopsora ampelospidis, Guignardia bidwellii, Plasmopara viticola*, persimon-tree: *Gloeosporium kaki, Cercospora kaki, Mycosphaerella nawae*, melon crops: *Colletotrichum lagenarium, Sphaerotheca fuliginea, Mycosphaerella melonis, Pseudoperonospora cubensis, Phytophthora sp.*, tomato: *Alternaria solani, Cladosporium fulvum, Phytophthora infestans*, egg plant: *Phomopsis vexans, Erysiphe cichoracaerum*, rape: *Alternaia japonica, Cercosporella brassicae*, welsh onion: *Puccinia allii*, soybean: *cercospora kikuchii, Elsinoe glycines,*

*Diaporthe phaseolorum var. sojae*, kidney bean: *Colletotrichum lindemuthianum*, peanut: *Mycosphaerella personatum, Cercospora arachidicola*, pea: *Erysiphe pisi*, potato: *Alternaria solani, Phytophthora infestans*, strawberry: *Sphaerotheca humuli*, tea: *Exobasidium reticulatum, Elsinoe leucospila*, tobacco-plant: *Alternaria longipes, Erysiphe cichoracearum, Colletotrichum tabacum, Peronospora tabacina, Phytophthora nicotianae*, sugar beet: *Cercospora beticola*, rose: *Diplocarpon rosae, Sphaerotheca pannosa*, chrysauthemum: *Septoria chrysanthemi-indici, Puccinia horiana*, crop plants: *Botrytis cinerea, Sclerotinia sclerotiorum*, and the like.

The acrylic acid derivatives (I) can be typically prepared by the methods as shown below:

The present compound can be obtained by (i) reacting esters of acetic acid derivative of the formula (II):

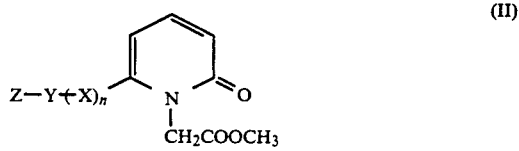

[wherein X, n, Y and Z are as defined above] with a formylating agent, a formyl compound-forming agent, to obtain the compound (III):

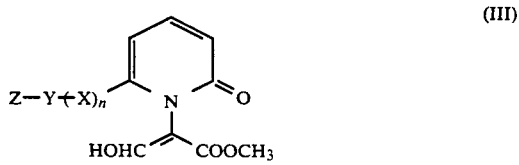

[wherein X, n, Y and Z are as defined above], (ii) followed by a treatment with a methylating agent, a methyl compound-forming agent.

In the reaction (i), examples of the formylating agent are formate esters, e.g. methyl formate and ethyl formate, formamides, e.g. N,N-dimethylformamide., etc.

This reaction is usually carried out in the presence of base at a temperature of about $-20°$ to $100°$ C. for a period of about 10 minutes to 2 hours. The formylating agent and the base are used at a proportion of 1 to 10 equivalents and about 1 to 2 equivalents, respectively, on the basis of one equivalent of the compound (II).

The reaction is usually carried out in a solvent. As the solvent, there may be exemplified aliphatic hydrocarbons, e.g. hexane and heptane, aromatic hydrocarbons, e.g. benzene and toluene, ethers, e.g. diisopropyl ether, dioxane, tetrahydrofuran and diethyl ether, halogenated hydrocarbons, e.g. chloroform, carbon tetrachloride and dichlorobenzene, acid amides, e.g. formamide and N,N-dimethylformamide, etc. and their mixtures. Examples of the base are sodium hydroxide, alkyl lithium, e.g. n-butyl-lithium, etc.

In the reaction (ii) (reaction of acrylic acid derivatives represented by the formula (III) with a methylating agent), examples of the methylating agent are methyl iodide, diazomethane and dimethylsulfuric acid.

This reaction is usually carried out in the presence of a base at a temperature of $-10°$ to $100°$ C. for a period of about 10 minutes to 24 hours. The methylating agent and the base may be used in an amount of 1 to 2 equivalents each on the basis of one equivalent of the compound (III).

Examples of the base are pyridine, 4-dimethylamino pyridine, triethylamine, N,N-dimethylaniline, sodium hydroxide, sodium hydride, potassium hydroxide, sodium carbonate or the like.

This reaction is usually carried out in a solvent. As the solvent, there may be exemplified aliphatic hydrocarbons, e.g. hexane and heptane, aromatic hydrocarbons, e.g. benzene and toluene, ethers, e.g. diisopropyl ether, dioxane, tetrahydrofuran and diethylether, halogenated hydrocarbons, e.g. chloroform, carbon tetrachloride and dichlorobenzene, acid amides, e.g. formamide and N,N-dimethylformamide, sulfur compounds, e.g. dimethyl sulfoxide and sulforan, nitriles, e.g. acetonitrile, ketones, e.g. acetone and methylisobutylkentone, alcohols, e.g. ethanol, water, etc. and their mixtures.

After completion of the reaction, the reaction mixture may be subjected to an after-treatment in a per se conventional manner such as extraction with an organic solvent and concentration. If necessary, any purification method, e.g. chromatography, recrystallization, etc., may be further adopted to give the objective compound (I). More easily, the above methods (i) and (ii) may be carried out without isolation of compound (iii).

Typical examples of the compounds (I) produced by the above procedures are shown in Table 1.

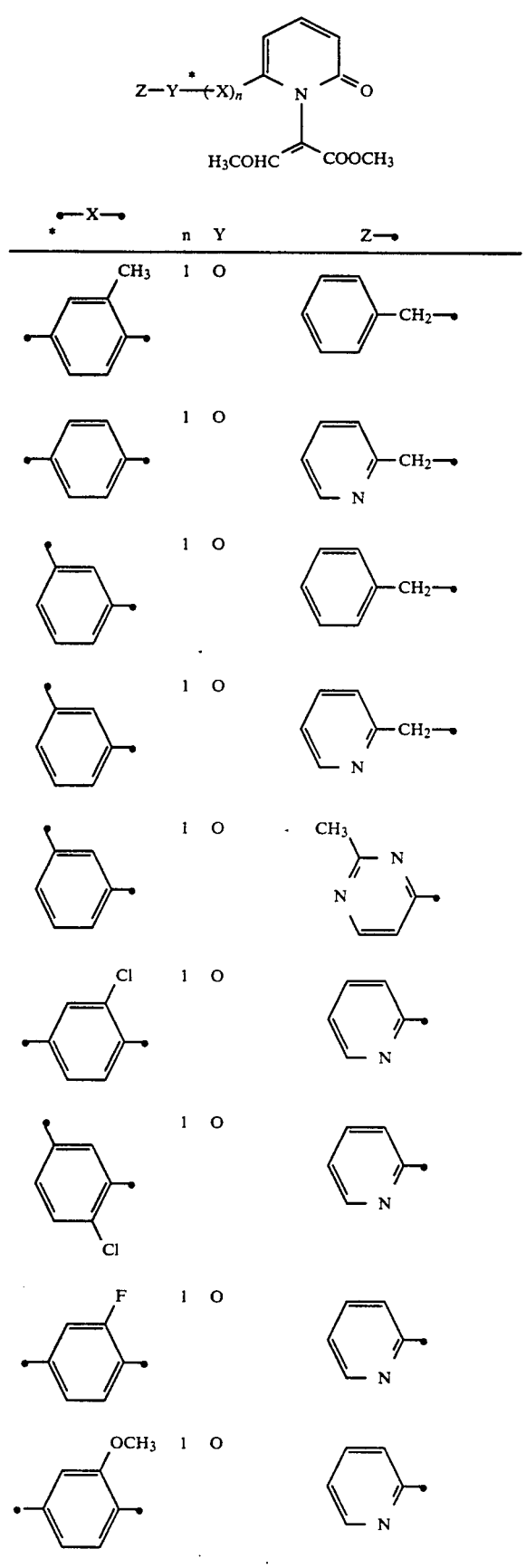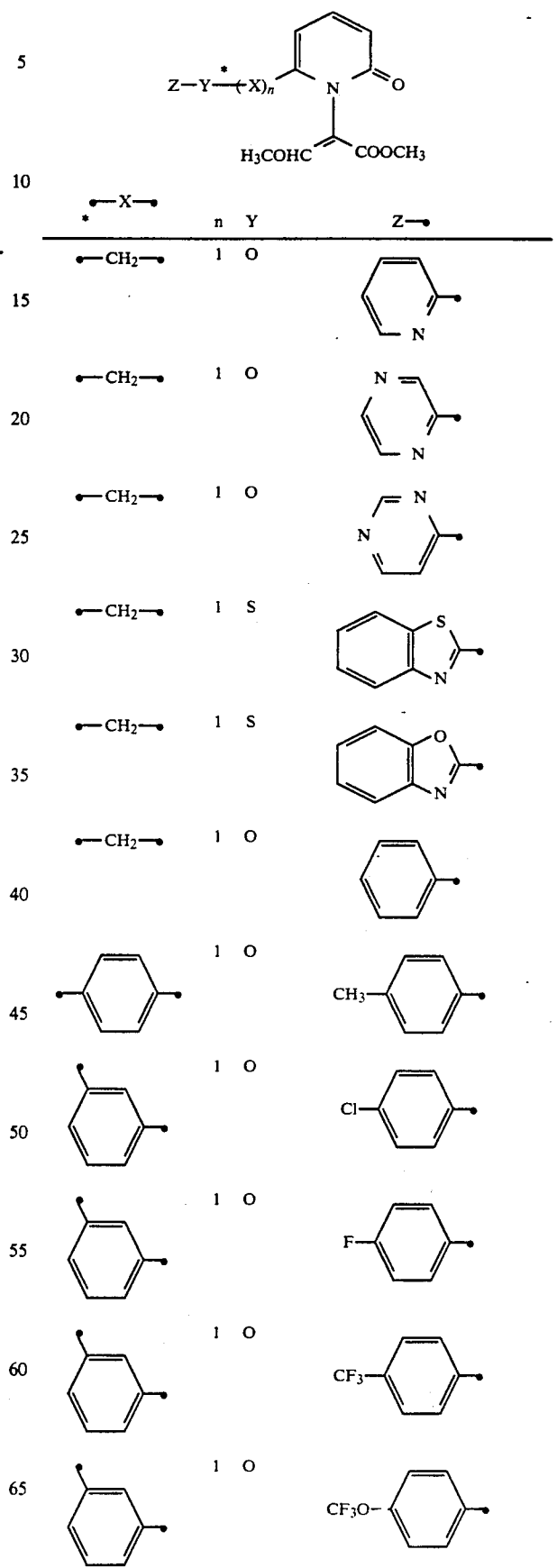

TABLE 1-continued
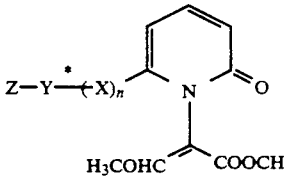
| ←X→ | n | Y | Z→ |
|---|---|---|---|
| 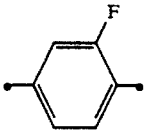 | 1 | O | 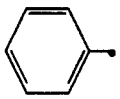 |
| 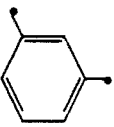 | 1 | O | 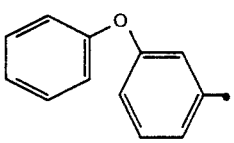 |
| 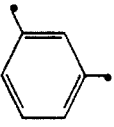 | 1 | O | 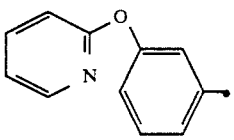 |
| 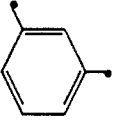 | 1 | O | 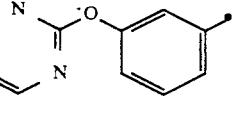 |
| 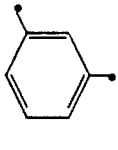 | 1 | O | 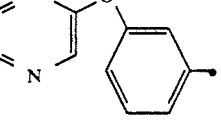 |
| 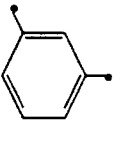 | 1 | O | 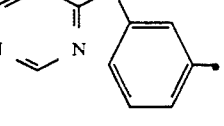 |
| — | 0 | O |  |
| — | 0 | O | 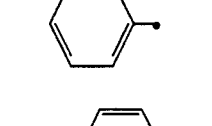 |
| — | 0 | O | 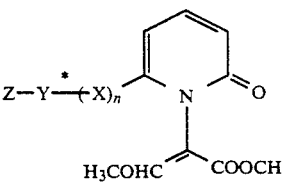 |
| — | 0 | O | 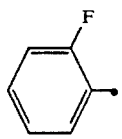 |
TABLE 1-continued
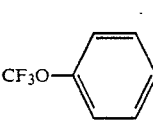
| ←X→ | n | Y | Z→ |
|---|---|---|---|
| — | 0 | O | 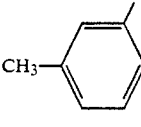 |
| — | 0 | O | 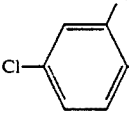 |
| — | 0 | O | 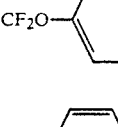 |
| — | 0 | O | 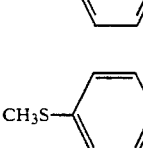 |
| — | 0 | O | 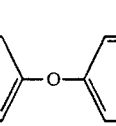 |
| — | 0 | O | 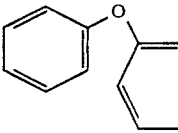 |
| — | 0 | O | 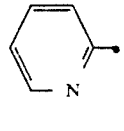 |
| — | 0 | O | 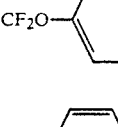 |
| — | 0 | O | 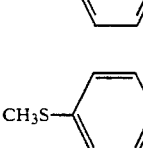 |
| — | 0 | O | 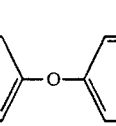 |

TABLE 1-continued

Z—Y—(X)ₙ—N(C=O pyridinone)  
H₃COHC=C(COOCH₃)

| —X— | n | Y | Z— |
|---|---|---|---|
| — | 0 | O | pyridin-3-yl |
| — | 0 | O | pyrimidin-2-yl |
| — | 0 | O | pyrazin-2-yl |
| — | 0 | O | 5-chloropyridin-2-yl |
| — | 0 | O | 5-(trifluoromethyl)pyridin-2-yl |
| — | 0 | O | benzyl |
| — | 0 | S | benzothiazol-2-yl |
| — | 0 | O | (pyridin-2-yl)methyl |
| — | 0 | O | 4-chlorobenzyl |
| — | 0 | O | 4-methylbenzyl |
| — | 0 | O | 4-fluorobenzyl |

TABLE 1-continued

Z—Y—(X)ₙ—N(C=O pyridinone)  
H₃COHC=C(COOCH₃)

| —X— | n | Y | Z— |
|---|---|---|---|
| — | 0 | O | (furan-2-yl)methyl |
| —CH₂— | 1 | O | 3-phenoxyphenyl |
| —CH₂— | 1 | O | 3-(pyridin-2-yloxy)phenyl |
| —CH₂— | 1 | O | 3-(pyrazin-2-yloxy)phenyl |
| —CH₂— | 1 | O | 3-(pyrimidin-4-yloxy)phenyl |
| — | 0 | O | 3-phenoxyphenyl |
| — | 0 | O | 3-(pyridin-2-yloxy)phenyl |
| — | 0 | O | 3-(pyridin-3-yloxy)phenyl |
| — | 0 | O | 3-(pyrazin-2-yloxy)phenyl |
| — | 0 | O | 3-(pyrimidin-4-yloxy)phenyl |
| — | 0 | O | 3-methylphenyl |

TABLE 1-continued
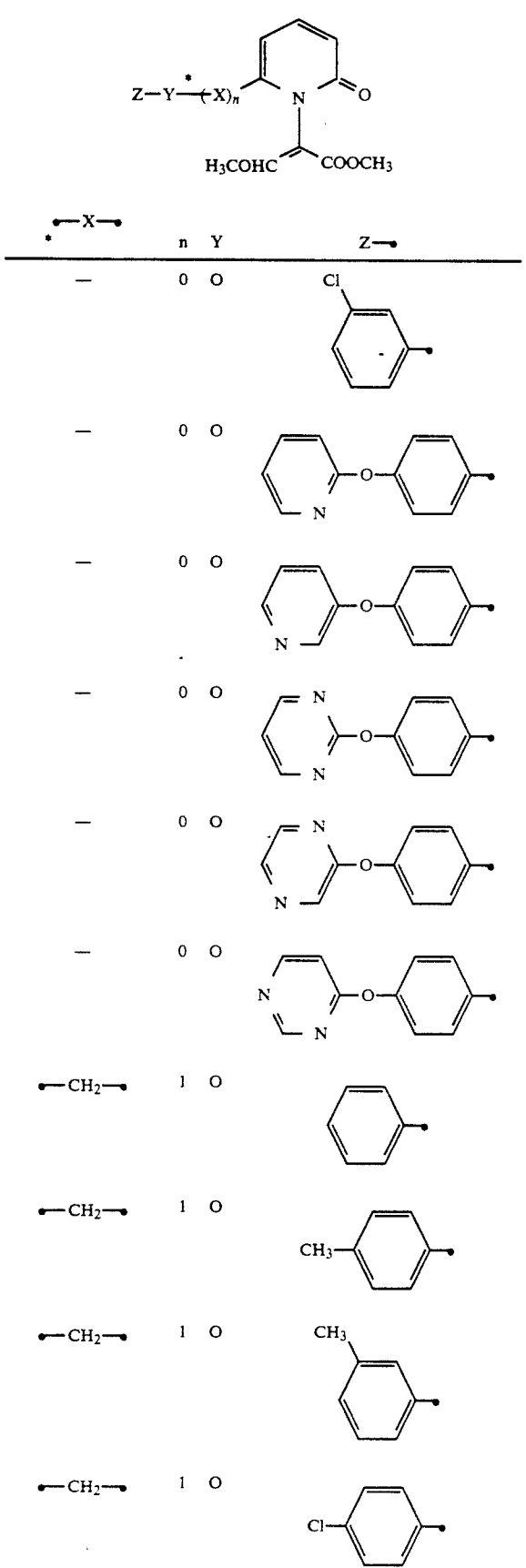
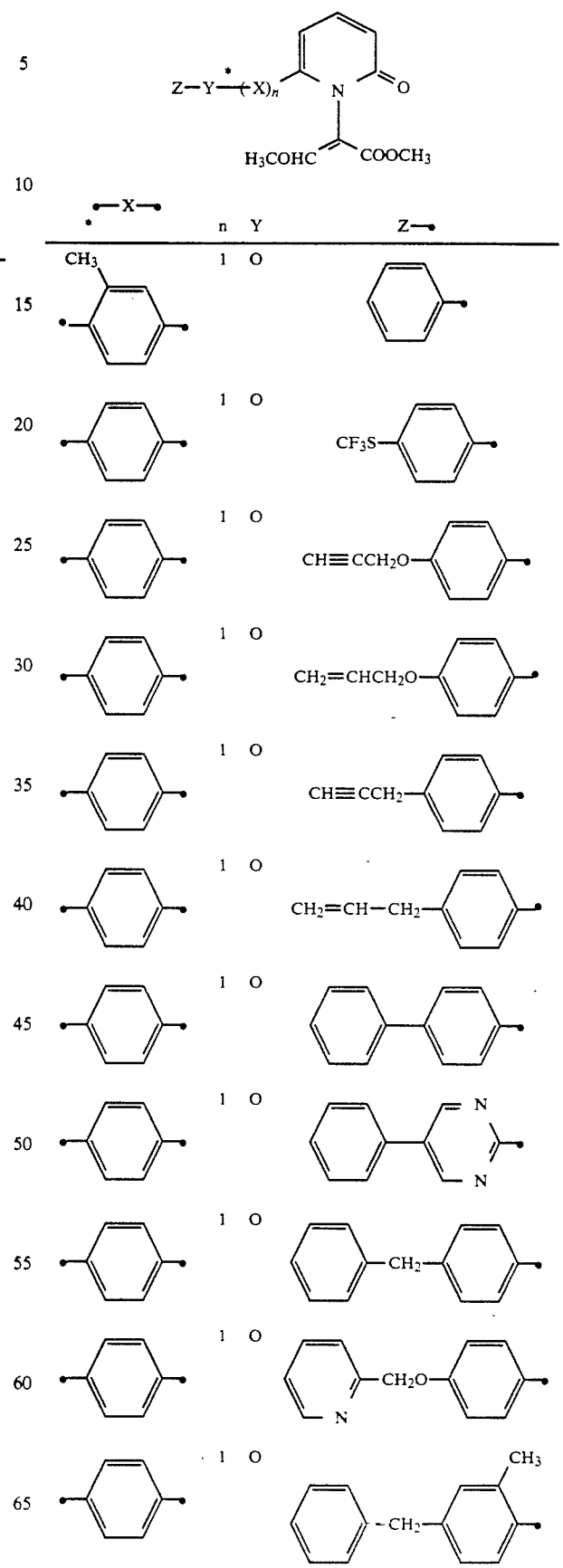

TABLE 1-continued

[Structure: Z—Y—*(X)ₙ—N-pyridone with H₃COHC=C(COOCH₃) substituent]

| —X— | n | Y | Z— |
|---|---|---|---|
| phenylene | 1 | O | 6-chloropyridazin-3-yl |
| phenylene | 1 | O | 6-phenoxypyridazin-3-yl |
| phenylene | 1 | O | 5,7-dimethylpyrazolo[1,5-a]pyrimidin-2-yl |
| phenylene | 1 | O | 5,7-dimethyl-[1,2,4]triazolo[1,5-a]pyrimidin-2-yl |
| phenylene | 1 | O | 4,6-dimethoxy-1,3,5-triazin-2-yl |
| phenylene | 1 | O | 4,6-dimethoxypyrimidin-2-yl |
| phenylene | 1 | O | quinazolin-2-yl |
| phenylene | 1 | O | quinoxalin-2-yl |
| phenylene | 1 | O | 4,6-bis(propargyloxy)pyrimidin-2-yl (CH≡CCH₂O-) |
| —CH₂— | 1 | O | 4-C₂H₅-phenyl |
| —CH₂— | 1 | O | 4-iso C₃H₇-phenyl |
| —CH₂— | 1 | O | 4-t C₄H₉-phenyl |
| —CH₂— | 1 | O | 4-n C₅H₁₁-phenyl |
| phenylene | 1 | O | 4-cyclopropyloxy-phenyl |
| phenylene | 1 | O | 4-iso C₃H₇O-phenyl |
| phenylene | 1 | O | 4-(CH≡CC(CH₃)HO)-phenyl |
| phenylene | 1 | O | 4-(CH≡CCH₂CH₂O)-phenyl |

In the above formulas, "." indicates bonding site and "*—" indicates bonding with Y site.

When X is a phenyl group which may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, the compound (II) is obtainable by reacting a compound of the formula (IV):

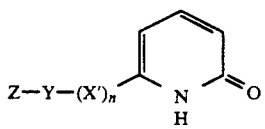

(IV)

wherein n, Y and Z are as defined above and X' is a phenyl group which may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, with a compound of the formula (V):

$$WCH_2COOCH_3 \quad (V)$$

wherein W is halogen, in the presence of a base.

This reaction is usually carried out at a temperature of −10° to 50° C. for a period of about 10 minutes to 24 hours. The compound (V) and the base may be used in an amount of 1 to 2 equivalents each on the basis of one equivalent of the compound (IV).

Examples of a base are pyridine, 4-dimethyl amino pyridine, triethylamine, N,N-dimethylaniline, sodium hydroxide, potassium hydroxide, sodium carbonate, sodium hydride or the like.

As the solvent, there may be exemplified aliphatic hydrocarbons, e.g. hexane and heptane, aromatic hydrocarbons, e.g. benzene and toluene, ethers, e.g. diethyl ether, diisopropyl ether, dioxane and tetrahydrofuran, halogenated hydrocarbons, e.g. chloroform, carbon tetrachloride and dichlorobenzene, acid amides, e.g. formamide and N,N-dimethylformamide, sulfur compounds, e.g. dimethylsulfoxide and sulforan, nitriles, e.g. acetonitrile, ketones, e.g. acetone and methylisobutylketone, alcohols, e.g. ethanol, water etc., and their mixtures.

After completion of the reaction, the reaction mixture may be subjected to an after-treatment in a per se conventional manner such as extraction with an organic solvent and concentration. If necessary, any purification method, e.g. chromatography, recrystallization, etc., may be further adopted to give the objective compound (II).

The pyridone derivatives represented by the formula (IV) wherein n is 1 is synthesized in accordance with the process described in Synthesis (1976), pp. 1–24. In detail, the derivatives represented by the formula (IV) is obtainable by reacting a Mannich base, which is obtainable by reacting optionally substituted acetophenone with agent, such as paraformaldehyde and dimethylamine hydrochloride, with pyridinium salts and ammonium salts (e.g. ammonium acetate.) The pyridinium salts mentioned above is obtainable by reacting pyridine and haloacetate ester. The pyridone derivatives represented by the formula (IV) wherein n is 0 is synthesized in accordance with the following schemes.

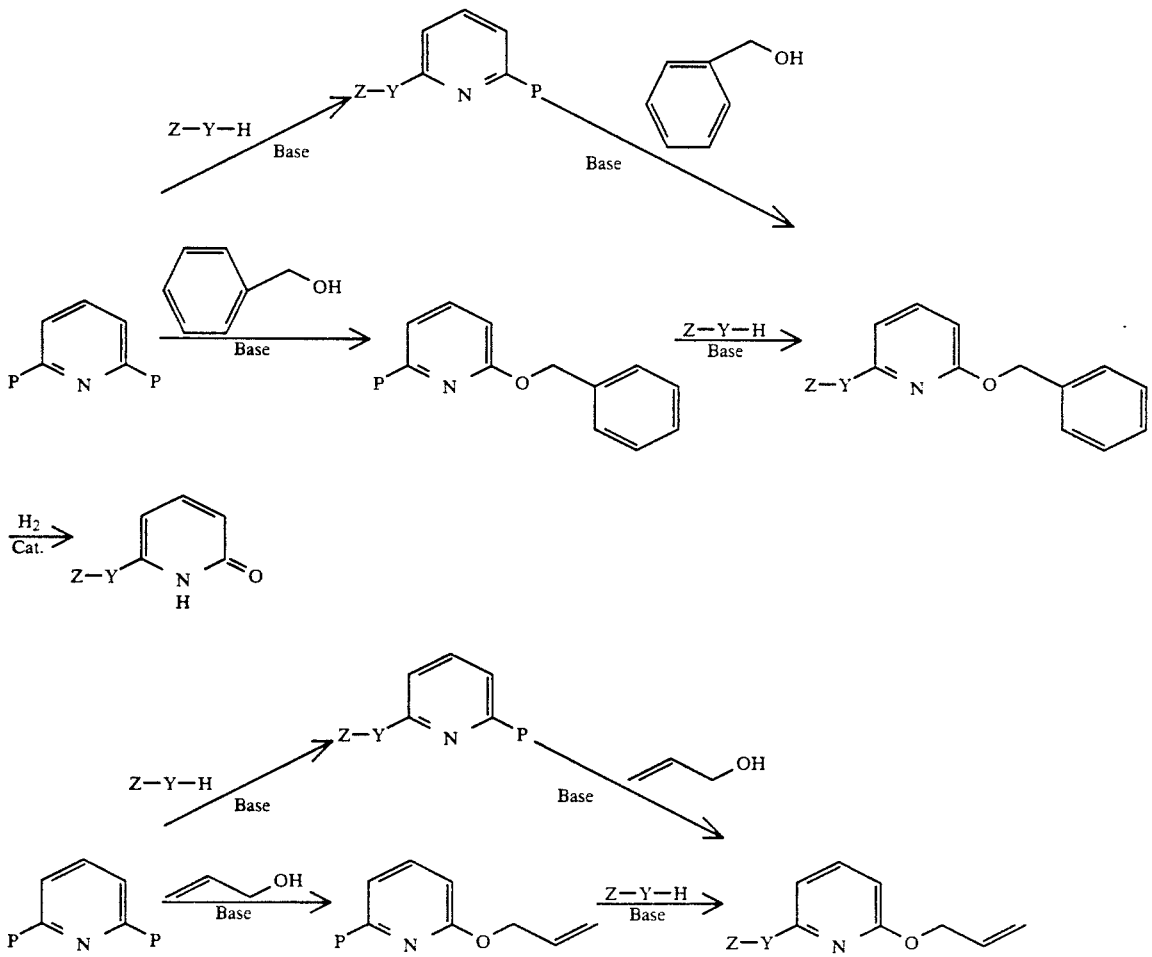

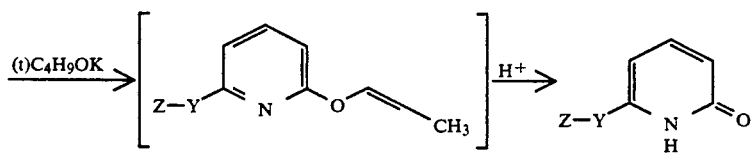

wherein Y and Z are as defined above and P represents halogen.

As generally known, some of the pyridone derivatives represented by the formula (IV) may be present as pyridinol derivatives represented by the following formula which are isomers of the pyridone derivatives or as mixtures thereof.

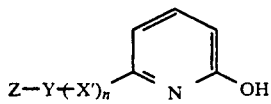

wherein X', n, Y and Z are as defined above.

Furthermore, the starting acetate derivatives represented by the formula (II) wherein n is 1 and X is a methylene group is obtained by allowing acetate derivatives represented by the formula (VI):

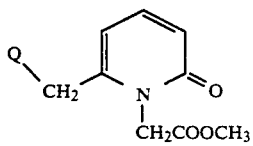 (VI)

wherein Q is a halogen atom, to react with derivatives represented by the formula (VII):

 (VII)

wherein Z and Y are as defined above, in the presence of a base.

This reaction is usually carried out in a solvent at a temperature of −10° to 50° C. for a period of about 10 minutes to 24 hours. The compound (VII) and the base may be used in an amount of 1 to 2 equivalents each on the basis of one equivalent of the compound (VI).

Examples of a base are pyridine, 4-dimethylamino pyridine, triethylamine and N,N-dimethylaniline, sodium hydroxide, sodium hydride, potassium hydroxide, sodium carbonate, silver carbonate or the like.

As the solvent, there may be exemplified aliphatic hydrocarbons, e.g. hexane and heptane, aromatic hydrocarbons, e.g. benzene and toluene, ethers, e.g. diethyl ether, diisopropyl ether, dioxane and tetrahydrofuran, halogenated hydrocarbons, e.g. chloroform, carbon tetrachloride and dichlorobenzene, acid amides, e.g. formamide and N,N-dimethylformamide, sulfur compounds, e.g. dimethylsulfoxide and sulforan, nitriles, e.g. acetonitrile, ketones, e.g. acetone and methylisobutylketone, alcohol, e.g. ethanol, water, etc. and their mixtures.

After completion of the reaction, the reaction mixture may be subjected to an after-treatment in a per se conventional manner such as extraction with an organic solvent and concentration. If necessary, any purification method, e.g. chromatography, recrystallization, etc., may be further adopted to give the objective compound (II).

The compounds of the formula (VI) are synthesized in accordance with the following scheme.

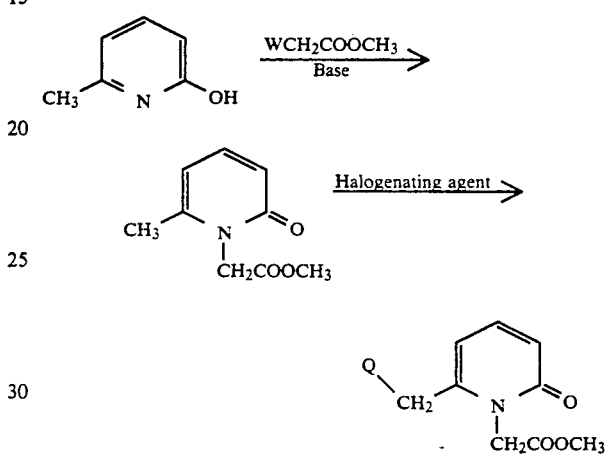

wherein W and Q each is a halogen atom.

For the practical usage of the acrylic acid derivatives (I), it is usually formulated with a conventional solid or liquid carrier(s) or diluent(s) as well as a surface active agent(s) or auxiliary agent(s) into a conventional preparation form such as emulsifiable concentrate, wettable powder, suspension, granules or dusts. The content of the acrylic acid compound (I) as the active ingredient in such preparation form is normally within a range of about 0.1 to 99.9% by weight, preferably of about 1 to 90% by weight. Examples of the solid carrier or diluent are fine powders or granules of kaolin clay, attapulgite clay, bentonite, terra alba, pyrophyllite, talc, diatomaceous earth, calcite, corncob powder, walnut shell powders, urea, ammonium sulfate and synthetic hydrous silica, etc. As the liquid carrier or diluent, there may be exemplified aromatic hydrocarbons, e.g. xylene and methylnaphthalene, alcohols, e.g. isopropanol, ethylene glycol and 2-ethoxyethanol, ketones, e.g. acetone, cyclohexanone and isophorone, vegetable oil, e.g. soybean oil and cotton-seed oil, dimethylsulfoxide, acetonitrile, water, etc.

The surface active agent used for emulsification, dispersing or spreading may be of any type, for instance, either anionic or non-ionic. Examples of the surface active agent include alkylsulfates, alkylsulfonates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agent include ligninsulfonates, alginate, polyvinyl alcohol, gum arabic, CMC (carboxymethyl cellulose), PAP (isopropyl acid phosphate), etc.

These formulations are used as such or after dilution with water for foliage application or soil treatment, soil incorporation or seed teatment. They may also be used in combination with other fungicide, an insecticide, acaricide, nematicide, herbicide, plant growth regulator, fertilizer or soil conditioner.

In the case where the present compound is used as an active ingredient of a fungicide, the dosage varies depending on the weather conditions, formulation, application time, application method, application place, object diseases and object crops. The dosage is usually 0.1 to 100 g, preferably 0.2 to 20 g for an area of 1 are. In the case of emulsion, wettable powder, suspension formulation which is diluted with water prior to application, the concentration should be 0.001 to 0.5%, preferably 0.0005 to 0.2% by weight. Granules and dusts are used as such without dilution.

The present invention is explained in further detail referring to synthesis examples, formulation examples and efficiency tests.

Synthesis Examples of the Present Compound

Synthesis Example 1

To a solution of methyl 2-[6-(4-pyridine-2-yloxy)phenyl-2-pyridone-1-yl]acetate (1 g) in dry N,N-dimethylformamide (5 ml) and methyl formate (1.8 g) was gradually added 60% oily sodium hydride (0.18 g) under ice cooling. After completion of foaming, temperature was cooled to room temperature and stirring was carried out for 6 hours. To the reaction mixture was added dimethyl sulfate (0.57 g), followed by stirring for 3 hours at room temperature. After completion of the reaction, the reaction mixture was charged into water (30 ml), followed by extraction with ether (50 ml×2). The ether layers were collected, washed with water, dried over anhydrous magnesium sulfate and concentrated under reduced pressure to obtain an oily residue. This was subjected to silica gel column chromatography (eluent; hexane: ethyl acetate=2:1 (V/V)) to obtain methyl 2-[6-(4-pyridine-2-yloxy)phenyl)-2-pyridone-1-yl]-3-methoxypropenoate (the present compound (1)) (0.7 g).

Synthesis Example 2

To a solution of methyl 2-[6-(3-methylphenoxy)-2-pyridone-1-yl]acetate (1 g) in dry N,N-dimethylformamide (5 ml) and methyl formate (2.2 g) was gradually added 60% oily sodium hydride (0.22 g) under ice cooling. After completion of foaming, temperature was cooled to room temperature and stirring was carried out for 12 hours. To the reaction mixture was added dimethyl sulfate (0.7 g), followed by stirring for 3 hours at room temperature. After completion of the reaction, the reaction mixture was charged into water (30 ml), followed by extraction with ether (50 ml×2). The ether layers were collected, washed with water, dried over anhydrous sodium sulfate and concentrated under reduced pressure. The resulting oily residue was subjected to silica gel column chromatography (eluent; hexane: ethyl acetate=2:1 (V/V)) to obtain methyl 2-[6-(3-methylphenoxy)-2-pyridone-1-yl]-3-methoxypropenoate (the present compound (5)) (0.7 g).

Synthesis Example 3

In the same manner as in the above two synthesis examples, methyl 2-[6-(3-methylphenoxymethyl)-2-pyridone-1-yl]-3-methoxypropenoate (the present compound (10)) (0.6 g) was obtained using methyl 2-[6-(3-methylphenoxymethyl)-2-pyridone-1-yl]-acetate (1 g) as a starting material.

The present compounds prepared in accordance with the above synthesis examples are shown in Table 2.

TABLE 2

Compound represented by the formula (I):

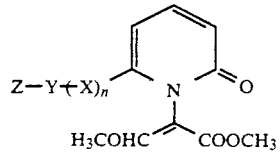

("•" indicates bonding site and "• —" indicates bond with Y side.)

| Compound No. | •—X—• | n | Y | Z—• | Properties | Isomers |
|---|---|---|---|---|---|---|
| (1) | (para-phenylene) | 1 | O | (pyridyl) | $n_D^{23.5}$ 1.6050 | (E) |
| (2) | (meta-phenylene) | 1 | O | (phenyl)-CH₂—• | $n_D^{25.0}$ 1.5788 | (E) |
| (3) | (meta-phenylene) | 1 | O | (pyridyl) | Glassy | (E) |

TABLE 2-continued

Compound represented by the formula (I):

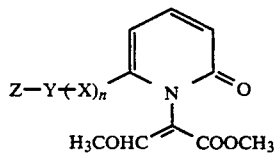

("●" indicates bonding site and "*●—" indicates bond with Y side.)

| Compound No. | ●—X—● | n | Y | Z—● | Properties | Isomers |
|---|---|---|---|---|---|---|
| (4) | — | 0 | O | phenyl | $n_D^{23.5}$ 1.5650 | (E) |
| (5) | — | 0 | O | 3-CH₃-phenyl | $n_D^{24.5}$ 1.5409 | (E) |
| (6) | — | 0 | O | 4-CF₃O-phenyl | $n_D^{23.5}$ 1.5072 | (E) |
| (7) | — | 0 | O | 2,4-(CH₃)₂-phenyl | $n_D^{22.5}$ 1.5446 | (E)/(Z) ≈ 4/1 |
| (8) | — | 0 | O | 2-pyridyl-CH₂—● | $n_D^{22.5}$ 1.5560 | (E) |
| (9) | — | 0 | O | 2-pyridyl-O-(4-phenyl)● | m.p. 134–135° C. | (E) |
| (10) | ●—CH₂—● | 1 | O | 3-CH₃-phenyl | $n_D^{23.5}$ 1.5412 | (E)/(Z) ≈ 5/1 |
| (11) | ●—CH₂—● | 1 | O | 2-pyridyl | $n_D^{24.0}$ 1.5485 | (E) |
| (12) | ●—CH₂—● | 1 | S | benzothiazol-2-yl | | (E) |
| (13) | 1,4-phenylene | 1 | O | 2-pyridyl-CH₂—● | m.p. 111–112.5° C. | (E) |

TABLE 2-continued

Compound represented by the formula (I):

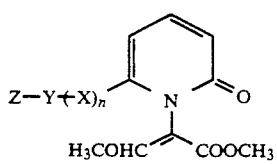

("•" indicates bonding site and "•—" indicates bond with Y side.)

| Compound No. | •—X—• | n | Y | Z—• | Properties | Isomers |
|---|---|---|---|---|---|---|
| (14) | para-phenylene | 1 | O | phenyl | $n_D^{22.5}$ 1.6098 | (E) |
| (15) | meta-phenylene | 1 | O | pyridin-2-yl-CH₂—• | | (E) |
| (16) | para-phenylene | 1 | O | phenyl-CH₂—• | m.p. 116–118° C. | (E) |

Synthesis examples of starting compounds used for preparing the present compounds are shown below.

Synthesis Examples of the Compound (III)

To a solution of methyl 2-[6-(4-(pyridine-2-yloxy)-phenyl)-2-pyridone-1-yl]acetate (1 g) in dry N,N-dimethylformamide (5 ml) and methyl formate (1.8 g) was gradually added 60% oily sodium hydride (0.18 g) under ice cooling. After completion of foaming, temperature was cooled to room temperature and stirring was carried out for 6 hours. To the reaction mixture was added 0.1N aqueous hydrogenchloride (4.5 ml), and water (30 ml), followed by extraction with ether (50 ml×2). The ether layers were collected, washed with water, dried over anhydrous magnesium sulfate and concentrated under reduced pressure to obtain an oily residue. This was subjected to silica gel column chromatography (eluent; hexane: ethyl acetate = 1:1 (V/V)) to obtain methyl 2-[6-(4-pyridine-2-yloxy)phenyl)-2-pyridone-1-yl]-3-hydroxy- propenoate (0.65 g).

Synthesis Examples of the Compounds (II), (IV) and (VI)

Example 1

Preparation of methyl 2-[6-(4-pyridine-2-yloxy)phenyl)-2-pyridone-1-yl]acetate (intermediate in Synthesis Example 1)

(a) 4'-Hydroxyacetophenone was condensed with 2-bromopyridine by Ullmann reaction to obtain 4'-(pyridine-2-yloxy)acetophenone (yield 73%). This was converted to Mannich base with dimethylamine hydrochloride and paraformaldehyde (yield 56%), which was then cyclized by reacting with 1-ethoxycarbonylmethylpyridinium chloride and ammonium acetate in N,N-dimethyl formamide, (as described in Synthesis (1976), pages 1-24) to obtain 6-[4-(pyridine-2-yloxy)phenyl]-2-pyridone (yield 32%).

(b) To a solution of the resulting 6-[4-(pyridine-2-yloxy)phenyl]-2-pyridone (3 g) in dry N,N-dimethylformamide (30 ml) was gradually added 60% oily sodium hydride (0.5 g) under ice cooling. After completion of foaming, to the reaction mixture were gradually added dry N,N-dimethylformamide (10 ml) and methyl bromoacetate (1.83 g). The temperature was cooled to room temperature and stirring was carried out for 30 minutes. The reaction mixture was charged into water (100 ml), followed by extraction with ether (100 ml×2). The ether layers were collected, washed with water, dried over anhydrous sodium sulfate and concentrated under reduced pressure. The resulting oily residue was subjected to silica gel column chromatography (hexane: ethyl acetate = 6:1 (V/V)) to obtain methyl 2-[6-(4-pyridine-2-yloxynophenyl)-2-pyridone-1-yl]acetate (3.3 g, yield 86%).

Example 2

Preparation of methyl 2-[6-(3-methylphenoxy)-2-pyridone-1-yl]acetate (intermediate in Synthesis Example 2)

(a) 2,6-Dibromopyridine was condensed with benzyl alcohol by Ullmann reaction to obtain 2-benzyloxy-6-bromopyridine (yield 76%). This was further condensed with m-cresol by Ullmann reaction to obtain 2-benzyloxy-6-(3-methylphenoxy)-pyridine (yield 83%), which was then subjected to catalytic reduction in the presence of a catalyst, 5% palladium-carbon, to obtain 6-(3-methylphenoxy)-2-pyridone (yield 96%).

(b) To a solution of the resulting 6-(3-methylphenoxy)-2-pyridone (2 g) in dry N,N-dimethylformamide (30 ml) was added 60% oily sodium hydride (0.44 g) under ice cooling. After completion of foaming, to the reaction mixture were gradually added dry N,N-dimethylformamide (10 ml) and methyl bromoacetate (1.6 g). The temperature was cooled to room temperature and stirring was carried out for 30 minutes. The reaction mixture was charged into water (100 ml), followed by extraction with ether (100 ml×2). The ether layers were collected, washed with water, dried over anhydrous magnesium sulfate and concentrated under reduced pressure. The resulting oily residue was subjected to silica gel column chromatography (eluent; hexane: ethyl acetate=6:1 (V/V)) to obtain methyl 2-[6-(3-methylphenoxy)-2-pyridone-1-yl]acetate (2.1 g, yield 77%).

Example 3

Preparation of methyl 2-[6-(3-methylphenoxymethyl)-2-pyridone-1-yl]acetate (intermediate in Synthesis Example 3)

(a) To a solution of 6-methyl-2-pyridinol (3 g) in dry N,N-dimethylformamide (30 ml) was gradually added 60% oily sodium hydride (1.21 g) under ice cooling. After completion of foaming, to the reaction mixture were gradually added dry N,N-dimethylformamide (10 ml) and methyl bromoacetate (4.42 g). The temperature was cooled to room temperature and stirring was carried out for 1 hour. The reaction mixture was charged into water (100 ml), followed by extraction with ether (100 ml×2). The ether layers were collected, washed with water, dried over anhydrous sodium sulfate and concentrated under reduced pressure. The resulting oily residue was subjected to silica gel column chromatography (hexane: ethyl acetate=4:1 (V/V)) to obtain methyl 2-(6-methyl-2-pyridone-1-yl)-acetate (2.8 g, yield 56%).

(b) To a solution of the resulting methyl 2-(6-methyl-2-pyridone-1-yl)-acetate (2 g) in carbon tetrachloride (30 ml) were added N-bromosuccinimide (2.95 g) and further triethylamine (0.1 ml), followed by heating under refluxing for 2 hours. After the reaction mixture was left to be cooled, insoluble matters were removed by filtration and the filtrate was washed with water (50 ml×2). The organic layer was dried over anhydrous magnesium sulfate and concentrated under reduced pressure. The resulting oily residue was subjected to column chromatography (hexane: ethyl acetate=4:1 (V/V)) to obtain methyl 2-(6-bromomethyl-2-pyridone-1-yl)-acetate (2.6 g, yield 91%).

(c) To a solution of m-cresol (0.84 g) in dry N,N-dimetylformamide (30 ml) was added 60% oily sodium hydride (0.34 g) under ice cooling. After completion of foaming, to the reaction mixture was added methyl 2-(6-bromomethyl-2-pyridone-1-yl)-acetate (2 g) obtained in the above (b), followed by heating at a temperature of about 100° C. for 30 minutes. The reaction mixture was left to stand in order to cool and was charged into water (100 ml), followed by extraction with ether (100 ml×2). The ether layers were collected, washed with water, dried over anhydrous magnesium sulfate and concentrated under reduced pressure. The resulting oily residue was subjected to silica gel column chromatography (hexane: ethyl acetate=4:1 (V/V)) to obtain methyl 2-[6-(3-methylphenoxymethyl)-2-pyridone-1-yl]-acetate (1.7 g, yield 77%).

Typical examples of the compound II, produced as above are shown in Table 3.

TABLE 3-continued $$\text{(II)}$$

Structure: pyridin-2(1H)-one with Z–Y–(X)$_n$– substituent at position 6 and –CH$_2$COOCH$_3$ on N.

| —X— | n | Y | Z— | Properties |
|---|---|---|---|---|
| — | 0 | O | 3-methylphenyl | |
| — | 0 | O | 4-(CF$_3$O)phenyl | |
| — | 0 | O | 2,4-dimethylphenyl | |
| — | 0 | O | pyridin-2-yl-CH$_2$— | |
| — | 0 | O | 2-(pyridin-2-yloxy)phenyl | |
| —CH$_2$— | 1 | O | 3-methylphenyl | |
| —CH$_2$— | 1 | O | pyridin-2-yl | m.p. 61.5° C.–62.5° C. |
| —CH$_2$— | 1 | S | benzothiazol-2-yl | |
| 1,4-phenylene | 1 | O | pyridin-2-yl-CH$_2$— | m.p. 83.3° C. |
| 1,4-phenylene | 1 | O | phenyl | |
| 1,3-phenylene | 1 | O | pyridin-2-yl-CH$_2$— | |

TABLE 3-continued

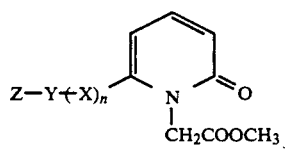

(II)

| —X— | n | Y | Z— | Properties |
|---|---|---|---|---|
| (p-phenylene) | 1 | O | benzyl-CH₂— | |
| (p-phenylene) | 1 | O | pyrazinyl | m.p. 93.3° C. |

Typical examples of the compound IV, produced as above are shown in Table 4.

TABLE 4

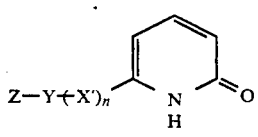

(IV)

| —X'— | n | Y | Z— |
|---|---|---|---|
| (p-phenylene) | 1 | O | 2-pyridyl |
| (m-phenylene) | 1 | O | benzyl-CH₂— |
| (m-phenylene) | 1 | O | 2-pyridyl |
| — | 0 | O | phenyl |
| — | 0 | O | m-tolyl (CH₃-phenyl) |
| — | 0 | O | 4-CF₃O-phenyl |

TABLE 4-continued (IV)

| —X'— | n | Y | Z— |
|---|---|---|---|
| — | 0 | O | 2,4-dimethylphenyl |
| — | 0 | O | 2-pyridyl-CH₂— |
| — | 0 | O | 2-pyridyl-O-phenyl |
| (p-phenylene) | 1 | O | 2-pyridyl-CH₂— |
| (p-phenylene) | 1 | O | phenyl |
| (m-phenylene) | 1 | O | 2-pyridyl-CH₂— |
| (p-phenylene) | 1 | O | benzyl-CH₂— |

TABLE 4-continued

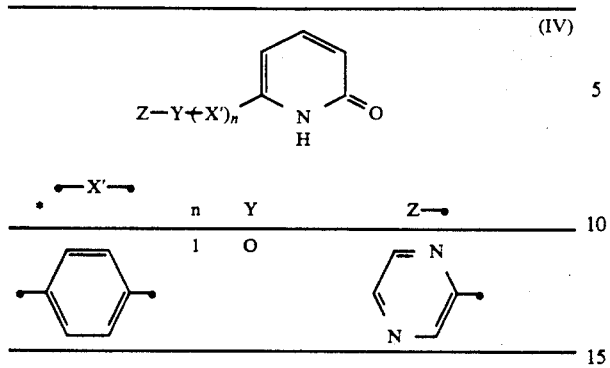

| •―X'―• | n | Y | Z―• |
|---|---|---|---|
| phenyl | 1 | O | pyrimidinyl |

FORMULATION EXAMPLES

The present compounds used are identified by numbers shown in Table 2. Quantities are expressed by parts by weight.

Formulation Example 1

A wettable powder each was prepared by mixing and pulverizing 50 parts of each of the present compounds (1)–(16), 3 parts of calcium ligninsulfonate, 2 parts of sodium lauryl sulfate and 45 parts of synthetic hydrated silica.

Formulation Example 2

A suspension each was prepared by mixing 25 parts of each of the present compounds (1)–(16), 3 parts of polyoxyethylene sorbitanmonooleate, 3 parts of CMC and 69 parts of water, followed by wet grinding to give a particle size smaller than 5 microns.

Formulation Example 3

A dust each was prepared by mixing and pulverizing 2 parts of each of the present compounds (1)–(16), 88 parts of kaolin clay and 10 parts of talc.

Formulation Example 4

An emulsifiable concentrate each was prepared by thoroughly mixing 20 parts of each of the present compounds (1)–(16), 14 parts of polyoxyethylene styrylphenyl ether, 6 parts of calcium dodecylbenzenesulfonate and 60 parts of xylene.

Formulation Example 5

A granule each was prepared by mixing and pulverizing 2 parts of each of the present compounds (1)–(16), 1 part of synthetic hydrated silica, 2 parts of calcium ligninsulfonate, 30 parts of bentonite and 65 parts of kaolin clay, followed by kneading with water, granulation and drying.

Formulation Example 6

An emulsifiable concentrate each was prepared by thoroughly mixing 10 parts of each of the present compounds (1)–(16), dissolved in 35 parts of xylene and 35 parts of dimethylformamide, with 14 parts of polyoxyethylene styrylphenyl ether and 6 parts of calcium dodecylbenzenesulfonate.

The following test examples demonstrate the effectiveness of the present compound used as an active ingredient of plant disease protectants. The present compounds used in the test examples are identified by the compound numbers shown in Table 2, and the compounds used for control are identified by the compound symbols shown in Table 3.

The controlling effect was evaluated by visually observing the degree of fungus colony and infected area of the leaves and stems of the test plants. The results of evaluation were expressed in terms of six ratings as follows:

"5" Not observed at all.
"4" Observed on about 10% of the leaves and stems.
"3" Observed on about 30% of the leaves and stems.
"2" Observed on about 50% of the leaves and stems.
"1" Observed on about 70% of the leaves and stems.
"0" Same as control.

The compounds as shown in Table 5 were used for comparison.

TABLE 5

| Compound No. | Chemical formula | Notes |
|---|---|---|
| (A) | (phenyl-pyridone with N–CH(OCH₃)COOCH₃ substituent) | Compound described in J2-121970A |

Test Example 1

Test for preventive controlling effect on speckled leaf blotch (*Septoria tritici*) of wheat Wheat seeds (var.: Norin No. 73) were sown in the sandy loam filled in a plastic pot. After raising for 8 days in a greenhouse, the seedlings were subjected to foliage application with a spray liquid of the emulsion prepared according to Formulation Example 4 which was diluted with water to the given concentration. After application, the seedlings were inoculated with spores of *Septoria tritici* by spraying a suspension of spores. The inoculated seedlings were grown in a dark damp place at 15° C. for 3 days, and then grown at 15° C. for 18 days under lighting, and the controlling effect was examined. The results are shown as follows.

Compound Nos. 1 and 13 showed "5" as controlling effect at each concentration of 200 and 12.5 ppm. On the other hand, compound (A) showed "0" as controlling effect at a concentration of 12.5 ppm.

Test Example 2

Test for preventive controlling effect on late blight (*Phytophthora infestans*) of tomato Tomato seeds (var.: Ponterosa) were sown in the sandy loam filled in a plastic pot. After raising for 20 days in a greenhouse, the seedlings were subjected to foliage application with a spray liquid of the wettable powder prepared according to Formulation Example 1 which was diluted with water to the given concentrations. After application, the seedlings were inoculated with *Phytophthora infestans* by spraying a suspension containing the spores. The inoculated seedlings were grown in a damp place at 20° C. for one day, and then grown in a greenhouse for 5 days, and the controlling effect was examined. The results are shown as follows.

Compound Nos. 1 and 13 showed "5" as controlling effect at a concentration of 200 ppm and further "4" as controlling effect of a concentration of 12.5 ppm. On the other hand, Compound (A) showed "0" as controlling effect at a concentration of 12.5 ppm.

Test Example 3

Test for preventive controlling effect on scab (*Venturia inaequalis*) of apple

Apple seeds (var.: Fuji) were sown in the sandy loam filled in a plastic pot. After raising for 20 days in a greenhouse, the seedlings, with the fourth to fifth foliage leaves open, were subjected to foliage application with a spray liquid of the suspension prepared according to Formulation Example 2 which was diluted with water to the given concentrations. After application, the seedlings were inoculated with spores of *Venturia inaequalis* by spraying a suspension containing the spores. The inoculated seedlings were grown in a dark damp place at 15° C. for 4 days, and then grown under lightening for 15 days. The controlling effect was examined. As a result, compound Nos. 1 to 16 showed more than 70% controlling effect against no treatment at a concentration of 2000 ppm.

Test Example 4

Test for preventive controlling effect on Grey mold (*Botrytis cinerea*) of cucumber Cucumber seeds (var.: Sagami hanjiro) were sown in the sandy loam filled in a plastic pot. After raising for 14 days in a greenhouse, the seedlings were subjected to foliage application with a spray liquid of the wettable powder prepared according to Formulation Example 1 which was diluted with water to the given concentrations. After application, the seedlings were air-dried and then inoculated with spores of Grey mold by spraying a suspension containing the spores. The inoculated seedlings were left to stand in a dark damp place at 15° C. for 3 day. The controlling effect was examined. The results are shown as follows.

Compound No. 13 showed "5" as controlling effect at a concentration of 50 ppm and further "4" as controlling effect at a concentration of 12.5 ppm. On the other hand, Compound (A) showed "0" as controlling effect at each concentration of 50 and 12.5 ppm.

We claim:

1. An acrylic acid compound of the formula (I):

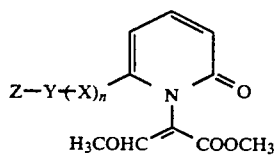

wherein X represents a phenyl group which may be substituted with one or two identical or different $C_1$-$C_5$ alkyl groups, $C_2$-$C_5$ alkenyl groups, $C_2$-$C_5$ alkynyl groups, $C_1$-$C_5$ alkoxy groups, $C_1$-$C_5$ haloalkyl groups, $C_1$-$C_5$ haloalkoxy groups, $C_1$-$C_5$ alkylthio groups, $C_1$-$C_5$ haloalkylthio groups or halogen atoms, or a methylene group, n represents 0 or 1, Y represents an oxygen atom or a sulfur atom, Z represents a phenyl group, an aralkyl group, an aromatic heterocyclyl group or an aromatic heterocyclylmethylene group containing an aromatic heterocyclyl group and Z may be substituted with one to three identical or different $C_1$-$C_5$ alkyl groups, $C_2$-$C_5$ alkenyl groups, $C_2$-$C_5$ alkynyl groups, $C_1$-$C_5$ alkoxy groups, $C_1$-$C_5$ haloalkyl groups, $C_1$-$C_5$ haloalkoxy groups, $C_3$-$C_5$ cycloalkyl groups, $C_1$-$C_5$ alkylthio groups, $C_1$-$C_5$ lower haloalkylthio groups or halogen atoms, or may be substituted with one substituent R in which R represents a phenyl group, a phenoxy group, an aralkyl group, an aralkyloxy group, an aromatic heterocyclyl group, an aromatic heterocyclyl oxy group containing an aromatic heteocyclyl group or an aromatic heterocyclylmethylene group containing an aromatic heterocyclyl group and R may be substituted with one or two identical or different $C_1$-$C_5$ alkyl groups, $C_2$-$C_5$ alkenyl groups, $C_2$-$C_5$ alkynyl groups, $C_1$-$C_5$ alkoxy groups, $C_1$-$C_5$ haloalkyl groups, $C_1$-$C_5$ haloalkoxy groups, $C_1$-$C_5$ alkylthio groups, $C_1$-$C_5$ haloalkylthio groups or halogen atoms, and the aromatic heterocyclyl group represented by Z and R, the aromatic heterocyclyl group in the aromatic heterocyclylmethylene group represented by Z and R, and the aromatic heterocyclyl group in the aromatic heterocyclyl oxy group represented by R are selected from the group consisting of a pyridinyl group, a pyrimidinyl group, a pyrazinyl group, a pyridazinyl group, a 1,2,4-triazinyl group, a 1,3,5-triazinyl group, a furyl group, a thienyl group, an oxazolyl group, a thiazolyl group, a quinolinyl group, an isoquinolinyl group, a quinoxalinyl group, a benzoxazolyl group, a benzothiazolyl group, a pyrazolo[1,5-a]pyrimidinyl group, and a triazolo[1,5-a]pyrimidinyl group.

2. An acrylic acid compound according to claim 1, wherein X is a phenyl group which may be substituted with one or two identical or different $C_1$-$C_5$ alkyl, $C_2$-$C_5$ alkenyl, $C_2$-$C_5$ alkynyl, $C_1$-$C_5$ alkoxy, $C_1$-$C_5$ haloalkyl, $C_1$-$C_5$ haloalkoxy, $C_1$-$C_5$ alkylthio or $C_1$-$C_5$ haloalkylthio groups or halogen atoms and n is 1.

3. An acrylic acid compound according to claim 2, wherein X is a phenyl group which may be substituted with one or two identical or different $C_1$-$C_5$ alkyl or $C_1$-$C_5$ haloalkyl groups or halogen atoms.

4. An acrylic acid compound according to claim 3, wherein X is a phenyl group which may be substituted with one or two identical or different $C_1$-$C_2$ alkyl groups, trifluoromethyl groups or halogen atoms.

5. An acrylic acid compound according to claim 4, wherein Y is an oxygen atom.

6. An acrylic acid compound according to claim 1, wherein Z is a phenyl group, an aralkyl group, an aromatic heterocyclyl group or an aromatic heterocyclylmethylene group containing an aromatic heterocyclyl group, all of which may be substituted with one to three identical or different $C_1$-$C_5$ alkyl, $C_1$-$C_5$ haloalkyl or $C_1$-$C_5$ haloalkoxy groups or halogen atoms.

7. An acrylic acid compound according to claim 6, wherein Z is a phenyl group, a benzyl group, a pyridyl group, a pyrimidinyl group, a pyrazinyl group or a pyridinylmethylene group, all of which may be substituted with one to three identical or different $C_1$-$C_2$ alkyl groups or halogen atoms.

8. An acrylic acid compound according to claim 7, wherein Y is an oxygen atom and X is a phenyl group, Z is a pyridyl group, pyridinylmethylene group, phenyl group or benzyl group and (Y-Z) group is at meta or para position.

9. An acrylic acid compound according to claim 8 wherein Z is a pyridyl group or pyridinylmethylene group.

10. A compound of the formula (III):

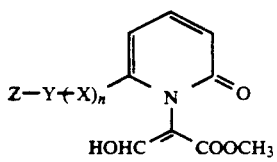

(III)

wherein X represents a phenyl group which may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, or a methylene group, n represents 0 or 1, Y represents an oxygen atom or a sulfur atom, Z represents a phenyl group, an aralkyl group, an aromatic heterocyclyl group or an aromatic heterocyclylmethylene group containing an aromatic heterocyclyl group and Z may be substituted with one to three identical or different lower alkyl groups, lower alkenyl groups, lower alkynyl groups, lower alkoxy groups, lower haloalkyl groups, lower haloalkoxy groups, cycloalkyl groups, lower alkylthio groups, lower haloalkylthio groups or halogen atoms, or may be substituted with one substituent R in which R represents a phenyl group, a phenoxy group, an aralkyl group, an aralkyloxy group, an aromatic heterocyclyl group, an aromatic heterocyclyl oxy group containing an aromatic heterocyclyl group or an aromatic heterocyclylmethylene group containing an aromatic heterocyclyl group and R may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, and the aromatic heterocyclyl group represented by Z and R, the aromatic heterocyclyl group in the aromatic heterocyclylmethylene group represented by Z and R, and the aromatic heterocyclyl group in the aromatic heterocyclyl oxy group represented by R are selected from the group consisting of a pyridinyl group, a pyrimidinyl group, a pyrazinyl group, a pyridazinyl group, a 1,2,4-triazinyl group, a 1,3,5-triazinyl group, a furyl group, a thienyl group, an oxazolyl group, a thiazolyl group, a quinolinyl group, an isoquinolinyl group, a quinoxalinyl group, a benzoxazolyl group, a benzothiazolyl group, a pyrazolo[1,5-a]pyrimidinyl group, and a triazolo[1,5-a]pyrimidinyl group.

11. A compound of the formula (II):

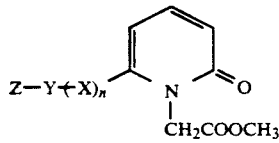

(II)

wherein X represents a phenyl group which may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, or a methylene group, n represents 0 or 1, Y represents an oxygen atom or a sulfur atom, Z represents a phenyl group, an aralkyl group, an aromatic heterocyclyl group or an aromatic heterocyclylmethylene group containing an aromatic heterocyclyl group and Z may be substituted with one to three identical or different lower alkyl groups, lower alkenyl groups, lower alkynyl groups, lower alkoxy groups, lower haloalkyl groups, lower haloalkoxy groups, cycloalkyl groups, lower alkylthio groups, lower haloalkylthio groups or halogen atoms, or may be substituted with one substituent R in which R represents a phenyl group, a phenoxy group, an aralkyl group, an aralkyloxy group, an aromatic heterocyclyl group, an aromatic heterocyclyl oxy group containing an aromatic heterocyclyl group or an aromatic heterocyclylmethylene group containing an aromatic heterocyclyl group and R may be substituted with one or two identical or different lower alkyl groups, lower alkenyl groups, lower alkynyl groups, lower alkoxy groups, lower haloalkyl groups, lower haloalkoxy groups, lower alkylthio groups, lower haloalkylthio groups or halogen atoms, and the aromatic heterocyclyl group represented by Z and R, the aromatic heterocyclyl group in the aromatic heterocyclylmethylene group represented by Z and R, and the aromatic heterocyclyl group in the aromatic heterocyclyl oxy group represented by R are selected from the group consisting of a pyridinyl group, a pyrimidinyl group, a pyrazinyl group, a pyridazinyl group, a 1,2,4-triazinyl group, a 1,3,5-triazinyl group, a furyl group, a thienyl group, an oxazolyl group, a thiazolyl group, a quinolinyl group, an isoquinolinyl group, a quinoxalinyl group, a benzoxazolyl group, a benzothiazolyl group, a pyrazolo[1,5-a]pyrimidinyl group, and a triazolo[1,5-a]pyrimidinyl group.

12. The acrylic acid compound according to claim 1 wherein the aromatic heterocyclyl group represented by Z and R, the aromatic heterocyclyl group in the aromatic heterocyclylmethylene group represented by Z and R, and the aromatic heterocyclyl group in the aromatic heterocyclyl oxy group represented by R are selected from the group consisting of a pyridinyl group, a pyrimidinyl group, a pyrazinyl group, a quinolinyl group, an isoquinolinyl group, a benzoxazolyl group, a benzothiazolyl group and a pyrazolo[1,5-a]pyrimidinyl group.

13. The acrylic acid compound according to claim 11 wherein the aromatic heterocyclyl group represented by Z and R, the aromatic heterocyclyl group in the aromatic heterocyclylmethylene group represented by Z and R, and the aromatic heterocyclyl group in the aromatic heterocyclyl oxy group represented by R are selected from the group consisting of a pyridinyl group, a pyrimidinyl group, a pyrazinyl group, a benzoxazolyl group and a benzothiazolyl group.

14. A compound of the formula (VI)

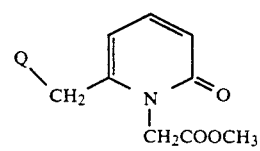

(VI)

wherein Q represents a halogen atom.

15. A compound of the formula

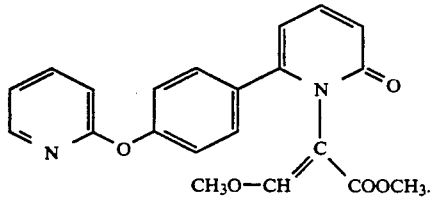

16. A compound of the formula

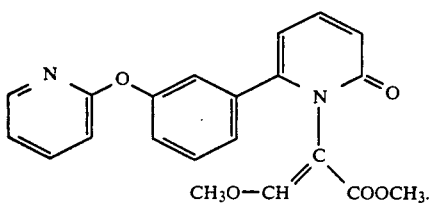

17. A compound of the formula

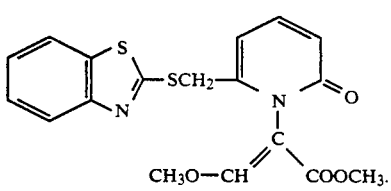

18. A compound of the formula

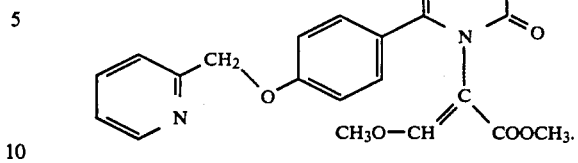

19. A compound of the formula

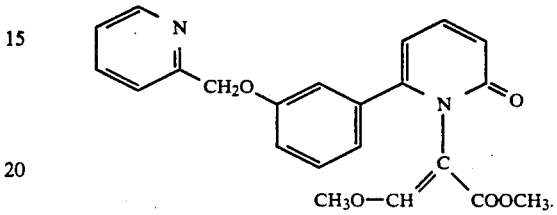

20. A compound of the formula

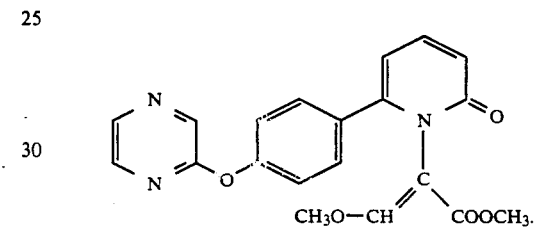

21. A compound of the formula

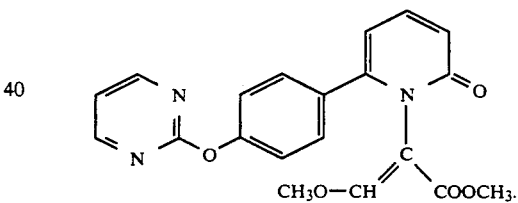

22. A fungicidal composition which comprises as an active ingredient a fungicidaly effective amount of the compound according to claim 1, and an inert carier or diluent.

23. A method for controlling plant pathogenic fungi which comprises applying a fungicidally effective amount of the compound according to claim 1 and an inert carrier or diluent to plant pathogenic fungi.

* * * * *